(12) United States Patent
Xiao et al.

(10) Patent No.: US 7,288,145 B2
(45) Date of Patent: Oct. 30, 2007

(54) PRECURSORS FOR DEPOSITING SILICON CONTAINING FILMS

(75) Inventors: Manchao Xiao, San Diego, CA (US); Arthur Kenneth Hochberg, Solana Beach, CA (US); Kirk Scott Cuthill, Vista, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 11/513,950

(22) Filed: Aug. 30, 2006

(65) Prior Publication Data

US 2007/0004931 A1   Jan. 4, 2007

Related U.S. Application Data

(62) Division of application No. 10/695,379, filed on Oct. 27, 2003, now Pat. No. 7,122,222.

(60) Provisional application No. 60/442,183, filed on Jan. 23, 2003.

(51) Int. Cl.
*C23C 16/34* (2006.01)
*C23C 16/40* (2006.01)

(52) U.S. Cl. .................. 106/287.11; 556/409; 556/413

(58) Field of Classification Search ........... 106/287.11; 556/409, 413
See application file for complete search history.

(56) References Cited

U.S. PATENT DOCUMENTS

| | | | |
|---|---|---|---|
| 4,577,039 A * | 3/1986 | Arkles et al. | 556/409 |
| 5,010,158 A | 4/1991 | Colombier et al. | |
| 5,066,734 A | 11/1991 | Colombier | |
| 5,234,869 A | 8/1993 | Mikata et al. | |
| 5,272,242 A | 12/1993 | Colombier | |
| 5,429,673 A * | 7/1995 | Peterson et al. | 106/287.11 |
| 5,616,754 A * | 4/1997 | Cruse et al. | 556/409 |
| 5,874,368 A | 2/1999 | Laxman | |
| 5,939,333 A | 8/1999 | Hurley et al. | |
| 5,976,991 A | 11/1999 | Laxman et al. | |
| 6,127,287 A | 10/2000 | Hurley et al. | |
| 6,146,938 A | 11/2000 | Saida et al. | |
| 6,204,206 B1 | 3/2001 | Hurley | |
| 6,284,583 B1 | 9/2001 | Saida et al. | |
| 6,350,708 B1 | 2/2002 | Hurley | |
| 6,365,231 B2 | 4/2002 | Sato et al. | |
| 6,503,557 B1 | 1/2003 | Joret | |
| 6,524,975 B2 | 2/2003 | Li et al. | |
| 2002/0076947 A1 | 6/2002 | Li et al. | |
| 2003/0215570 A1 | 11/2003 | Seutter et al. | |
| 2005/0048204 A1 | 3/2005 | Dussarrat et al. | |
| 2005/0109276 A1 | 5/2005 | Iyer et al. | |
| 2005/0199945 A1 | 9/2005 | Kodama et al. | |
| 2006/0009041 A1 | 1/2006 | Iyer et al. | |

FOREIGN PATENT DOCUMENTS

| JP | H0251530 | 2/1990 |
|---|---|---|
| JP | 03 006566 A | 1/1991 |
| JP | 06132284 | 5/1994 |
| JP | 2000 080476 | 3/2000 |

OTHER PUBLICATIONS

G.E. McGuire, Semiconductor Materials and Process Technology Handbook, Noyes Publication, (1988), no month provided, pp. 289-301.
Stanley Wolf, Silicon Processing for the VLSI Era, Lattice Press, (1990), no month provided, vol. II, pp. 20-22; 327-331.
Tetsuji Sorita, Mass Spectrometric and Kinetic Study of Low-Pressure . . . , J. Elect. Soc., (1994), no month provided, vol. 141, pp. 3505-3511.
B.A. Scott, Preparation of Silicon Nitride with Good Interface Properties . . . , Chemtronics, (1989), no month provided, vol. 4, pp. 231-234.
J.M. Grow, Growth Kinetics and Characterization of Low Pressure . . . , Elsevier Sci., (1995), no month provided, Mat. Letters 23, pp. 187-193.
W.C. Yeh, Low-Temperature Chemical-Vapor-Deposition of Silicon-Nitride . . . , J. Appl. Phys., (1996), no month provided, vol. 35, pp. 1509-1512.
Arthur K. Hochberg, Diethylsilane As A Silicon Source for the Deposition . . . , Mat. Res. Soc. Symp., (1991), no month provided, vol. 204, pp. 509-514.
Roy G. Gordon, Silicon Dimethylamido Complexes and Ammonia . . . , Chem. Mater., (1990), no month provided, 2, pp. 480-482.
Z.I. Sergeeva, Synthesis of Alkyl- and Dialkyl-Bis-(1,1-Dialkylhydrazino)-Silanes, J. Gen. Chem. of USSR, (1960), no month provided, vol. 30, pp. 716-717.
Z.I. Sergeeva, Reaction of Unsymmetrical and Dialkylhydrazines . . . , J. Gen. Chem. of USSR, (1963), no month provided, 33, pp. 1823-1826.
Marcus Soldner, Isomeric Cyclic Disilanedlyl Dimethylhydrazines, Inorg. Chem., (1998), no month provided, 37, pp. 601-603.
Norbert Mitzel, Two Different Cyclization Modes in the Formation of Silylhydrazines, Organometallics, (1993), no month provided, 12, pp. 413-416.
Norbert Mitzel, Cyclic Silylhydrazines and Their Borane Adducts, Inorg. Chem., (1995), no month provided, 34, pp. 4840-4845.

(Continued)

Primary Examiner—David M. Brunsman
(74) Attorney, Agent, or Firm—Joseph D. Rossi (57) ABSTRACT

A precursor composition is disclosed for use in the chemical vapor deposition of a material selected from the group consisiting of silicon oxynitride, silicon nitride, and silicon oxide. The composition comprises a hydrazinosilane of the formula:

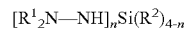

$[R^1_2N-NH]_n Si(R^2)_{4-n}$ where each $R^1$ is independently selected from alkyl groups of $C_1$ to $C_6$; each $R^2$ is independently selected from the group consisting of hydrogen, alkyl, vinyl, allyl, and phenyl; and n=1-4.

19 Claims, 6 Drawing Sheets

OTHER PUBLICATIONS

Seiichi Takami, Monolayer Nitridation of Silicon Surfaces by A Dry Chemical . . . , Appl. Phys. Lett., (1995), no month provided, 66, (12) pp. 1527-1529.

David R. Lide, Handbook of Chem. and Physics, 81st Edition, (2001), no month provided, CRC Press, pp. 9-64-9-69.

George Gibson, et al, "Reaction of Silicon Tetrachloride With N, N-dimethylhydrazine and Hydrazin," Inorg. Chem., (1963), no month provided, p. 876-8, vol. 2(4) ABSTRACT.

S.I. Sergeeva, et al, "Synthesis of Alkyl-and dialkylbis . . . silanes," Zhurnal Obshchei Khimii, (1960), no month provided, p. 694-5, vol. 30(2) ABSTRACT.

M.G. Voronkov, et al, "Silyl Derivatives of Asymmetric Dimethylhydrazine as . . . ," Izvestiya Vysshikh Uchebnykh Zavedenii, (2002), no month provided, p. 57-60, vol. (4) ABSTRACT.

Fomina, A. N., et al., Hydrosilylation of Methylhydrosilyl Derivatives of 1,1-Dimethylhydrazine, Russian Journal of General Chemistry, vol. 72, No. 1 (2002) pp. 53-54. Translation from Zhurnal Obshchei Khimii, vol. 72, No. 1, 2002, pp. 59-60.

* cited by examiner

"A" = Bis(DMH)methylsilane, $E_A$ = 39.8 kcal/mol, R.I. = 1.69
"C" = Tris(DMH)t-butylsilane, $E_A$ = 28.6 kcal/mol, R.I. = < 1.60 (est)
"E" = Tris(DMH)ethylsilane, $E_A$ = 26.3 kcal/mol, R.I. = 1.63
"F" = Bis(DMH)ethylsilane, $E_A$ = 35.8 kcal/mol, R.I. = 1.67

R.I. for 2:1 $NH_3$, 550°C dep, 632.8 nm

PRECURSORS FOR DEPOSITING SILICON CONTAINING FILMS

CROSS-REFERENCE TO RELATED APPLICATIONS

This application is a divisional application of U.S. patent application Ser. No. 10/695,379, filed on Oct. 27, 2003 now U.S. Pat. 7,122,222, which, in turn, claims the benefit of priority under 35 U.S.C. §119(e) to U.S. Provisional Application No. 60/442,183, filed on Jan. 23, 2003.

BACKGROUND OF THE INVENTION

The present invention relates to a class of novel precursors for chemical vapor deposition of silicon nitride, silicon oxide, and silicon oxynitride. In particular, the present invention relates to the synthesis of hydrazinosilanes and their applications as low temperature CVD precursors for silicon dielectric films in the fabrication of integrated circuit devices. These precursors may also be used for atomic layer deposition, plasma enhanced chemical vapor deposition, and atmospheric pressure chemical vapor deposition.

Silicon-containing dielectric depositions play an important role in the fabrication of integrated circuits. Silicon nitride can be used on semiconductor devices as diffusion barriers, gate insulators, for trench isolation, and capacitor dielectrics. Low temperature CVD process is the method widely accepted by semiconductor industry for silicon nitride film fabrication.

In the fabrication of semiconductor devices, a thin passive layer of a chemically inert dielectric material such as, silicon nitride ($Si_3N_4$) is essential. Thin layers of silicon nitride function as diffusion masks, oxidation barriers, intermetallic dielectric material with high dielectric breakdown voltages and passivation layers. The nitride films are used as sidewall spacers in MOS devices and, with oxides, and oxynitrides, gate dielectrics for Groups IV and II-V transistors. Many other applications of silicon-containing dielectric in the fabrication of semiconductor devices are reported elsewhere, see Semiconductor and Process technology handbook, edited by Gary E. McGuire, Noyes Publication, N.J., (1988), pp 289-301; and Silicon Processing for the VLSI ERA, Wolf, Stanley, and Talbert, Richard N., Lattice Press, Sunset Beach, Calif. (1990), pp 20-22, 327-330.

The present semiconductor industry standard silicon nitride growth method is by low pressure chemical vapor deposition in a hot wall reactor at >750° C. using dichlorosilane and ammonia.

Deposition of silicon nitride over large numbers of silicon wafers has been accomplished using many precursors. The low pressure chemical vapor deposition (LPCVD) using dichlorosilane and ammonia requires deposition temperatures greater than 750° C. to obtain reasonable growth rates and uniformities. Higher deposition temperatures are typically employed to get the best film properties. There are several drawbacks in these processes and some of these are as follows:

i) Silane and dichlorosilane are pyrophoric, toxic compressed gases; and
ii) Films from dichlorosilane have contaminants, such as chlorine and ammonium chloride, which are formed as byproducts.

Several classes of chemicals are used as precursors for silicon nitride film deposition. Among them are silanes, chlorosilanes, polysilazanes, aminosilanes, and azidosilanes.

Japanese Patent 6-132284 describes deposition of silicon nitride using organosilanes with a general formula $(R_1R_2N)_n SiH_{4-n}$ (where $R_1$ and $R_2$ range from H—, $CH_3$—, $C_2H_5$—, $C_3H_7$—, iso-$C_4H_9$—) by a plasma enhanced chemical vapor deposition and thermal chemical vapor deposition in the presence of ammonia or nitrogen. The precursors described here are tertiary amines and do not contain NH bonding as in the case of the present invention. The deposition experiments were carried out in a single wafer reactor at 400° C. at high pressures of 80-100 Torr. The Si:N ratios in these films were 0.9 (Si:N ratios in $Si_3N_4$ films is 0.75) with hydrogen content in the deposited films.

Sorita et al., J. Electro.Chem. Soc. Vol 141, No 12, (1994), pp 3505-3511, describe deposition of silicon nitride using dichlorosilane and ammonia using a LPCVD process. The major products in this process are aminochlorosilane, silicon nitride and ammonium chloride. Formation of ammonium chloride is a major drawback of using Si—Cl containing precursors. The formation of ammonium chloride leads to particle formation and deposition of ammonium chloride at the backend of the tube and in the plumbing lines and the pumping system. Processes which contain chlorine in the precursors result in $NH_4Cl$ formation. These processes require frequent cleaning and result in large down time of the reactors.

B. A. Scott, J. M. Martnez-Duart, D. B. Beach, T. N. Nguyen, R. D. Estes and R. G. Schad., Chemtronics, 1989, Vol 4, pp 230-234., report deposition of silicon nitride using silane and ammonia by LPCVD in the temperature region of 250-400° C. Silane is a pyrophoric gas and is difficult to control for the deposition of clean silicon nitride due to partial gas phase reaction.

J. M. Grow, R. A. Levy, X. Fan and M. Bhaskaran, Materials Letters, 23, (1995), pp 187-193, describe deposition of silicon nitride using ditertiarybutylsilane and ammonia by LPCVD process in the temperature range of 600-700° C. The deposited silicon nitride films were contaminated with carbon impurities (10 atomic %). This is mainly due to the presence of direct Si—C bonds in the precursor.

W-C. Yeh, R. Ishihara, S. Moishita, and M. Matsumura, Japan. J. Appl. Phys. 35, (1996) pp 1509-1512, describe a low temperature deposition of a silicon-nitrogen film using hexachlorodisilane and hydrazine near 350° C. The films are unstable in air and slowly convert to a silicon-oxygen film.

A. K. Hochberg and D. L. O'Meara, Mat. Res. Soc. Symp. Proc,. Vol. 204, (1991), pp 509-514, report deposition of silicon nitride and silicon oxynitride by using diethylsilane with ammonia and nitric oxide by LPCVD. The deposition was carried out in the temperature range of 650° C. to 700° C. The deposition is limited to deposition at 650° C. and the deposition rate drops to below 4 Å/min at lower temperatures. In the LPCVD process, precursors which contain direct Si—C carbon bonds result in carbon contamination in the films. Carbon free deposition requires greater than 5:1 $NH_3$ to precursor ratios. At lower ammonia concentrations, the films were found to contain carbon. Diethylsilane and ammonia processes typically require covered boats or temperature ramping to improve uniformities across the wafers.

U.S. Pat. No. 5,234,869 and R. G. Gordon and D. M. Hoffman, Chem. Mater., Vol. 2, (1990), pp 482-484 disclose other attempts to reduce the amount of carbon involved aminosilanes, such as tetrakis(dimethylamino)silane. The temperature of deposition is in the range of 300-1000° C. with pressures in the range of 1 mTorr-10 Torr. The presence of direct Si—N bonds and the absence of Si—C bonds were expected to give lower carbon concentrations in the films. However, there are three main disadvantages with precursors of this class.

1) They contain N-methyl groups, the methyl groups tend to migrate to the silicon surface readily and contaminate the films with carbon during a CVD process. In order to reduce the amount of carbon, the process involves high temperatures (>700) and high ammonia ratios (>10:1). With increased ammonia ratios the deposition rates dramatically reduce due to reactant depletion.
2) They do not contain NH bonding and they do not involve secondary silanes.
3) At lower temperatures the deposition rates and uniformities are very poor (>5%).

U.S. Pat. No. 5,874,368 describes our previous work to reduce the nitride deposition temperature to below 550° C. using bis(tertarybutylamino)silane ("BTBAS"). This temperature is still too high for depositions on circuits with metallization and on many Group III-V and II-VI devices. In addition, the precursor has a high activation energy that makes the process very temperature sensitive.

The trend of miniaturization of semiconductor devices and low thermal budget requires lower process temperature and higher deposition rate. A process involve a typical precursor such as BTBAS requires process temperature at least 550° C. Chlorosilanes need temperature even higher.

Ammonia plays an important role in silicon nitride CVD as nitrogen source. Hydrazine and its derivatives have been used as reagent for silicon surface nitradation[6-10], and also been used to replace ammonia as nitrogen source to react with chlorosilanes[11-13].

Although hydrazinosilanes were first synthesized several decades ago[1-2], very little research works have been conducted in this field. Some researchers have been interested in the chemistry of cyclic hydrazinosilanes in recent years[3-5]. However, in general those cyclic hydrazinosilanes have high molecular weight and, therefore, high boiling point. The high boiling point, or low vapor pressure, would be less preferred for CVD applications. No silicon-containing dielectric application of hydrazinosilanes has been published, especially for the open chain hydrazinosilanes.

The unusual reactivity of hydrazinosilanes is generally attributed to the weakness of the N—N bond linkage and hence the case with which it is homolytically cleaved.

The bond energy of N—N bond in 1,1-dimethylhydrazine (246.9 kJ/mol) is much less than that of Si—H bond in Me3SiH (377.8 kJ/mol), Si—C bond in s-Bu-SiMe3 (414 kJ/mol), and N-C bond in t-butylamine (362 kJ/mol)[15].

The present invention has overcome the problems of the prior art with the use of a group of precursors unique to the formation of silicon-containing dielectric films that are grown at low thermal conditions (to below 400° C.), have reduced carbon contamination, and have low hydrogen contamination. In addition, the precursors have very low activation energies that make processing less temperature sensitive, avoiding chlorine contamination and operate over a wide range of pressures ($10^{-5}$ Torr-760 Torr) in a manufacturing batch furnace or a single wafer reactor as will be described in greater detail below.

BRIEF SUMMARY OF THE INVENTION

The present invention provides a precursor composition for use in the chemical vapor deposition of a material selected from the group consisting of silicon oxynitride, silicon nitride, and silicon oxide, the composition comprising: a hydrazinosilane of the formula:

where each $R^1$ is independently selected from alkyl groups of $C_1$ to $C_6$; each $R^2$ is independently selected from the group consisting of hydrogen, alkyl, vinyl, allyl, and phenyl; and n=1-4.

DETAILED DESCRIPTION OF THE INVENTION

A large variety of "thin films" are used in the fabrication of Very Large Scale Integration (VLSI) devices. These deposited thin films can be of metals, semiconductors, or insulators. The films may be thermally grown or deposited from the vapor phase using LPCVD). VLSI technology requires very thin insulators for a variety of applications in both microprocessors and random-access memories device fabrication. Silicon dioxide has been predominantly used as a dielectric material because of its ease of deposition and excellent properties at the $SiO_2$/Si interface. Silicon nitride has other advantages over silicon dioxide, some of these include impurity and dopant resistant diffusion barriers, high dielectric breakdown voltages, superior mechanical properties and inherent inertness of $Si_3N_4$. Silicon oxynitride has improved electrical characteristics in certain applications.

In VLSI fabrication a large set of rigorous chemical, structural, process and electrical requirements need to be satisfied. Purity of the film, thickness, uniformity and deposition rates are some of the strictly controlled parameters to facilitate fabrication of submicron features in a device. It is a major advantage in the fabrication and performance of a device if the deposition process can be carried out at temperatures lower than 850° C. Silicon source materials for depositing silicon nitride under LPCVD conditions at these temperatures are limited to silane and dichlorosilane. A safe, reliable low temperature silicon nitride source material has applications in other technologies, such as; flat panel display devices, other electronic and non-electronic substrates or compound semiconductor device fabrication.

The present invention establishes that hydrazinosilanes are volatile enough to be delivered as CVD precursors, and they can form silicon-containing dielectric films at relatively low temperature. The deposition rate is significantly higher than that of aminosilanes. In addition, the effect on the silicon nitride film deposition rate from hydrazinosilanes by temperature change is much less than that of aminosilanes. This feature would improve the film uniformity when there is temperature variation across the wafer.

Processes that the hydrazinosilanes of the present invention can be used for include, the deposition of materials selected from the group consisting of silicon oxide, silicon oxynitride, and silicon nitride by chemical vapor deposition (CVD), plasma enhanced chemical vapor deposition (PECVD), low pressure chemical vapor deposition (LPCVD) and atomic layer deposition (ALD).

The present invention comprises a silicon nitride, silicon oxide or silicon oxynitride deposition process using a class of hydrazinosilanes represented by the formula:

where each $R^1$ is independently selected from alkyl groups of $C_1$ to $C_6$; each $R^2$ is independently selected from the group consisting of hydrogen, alkyl, vinyl, allyl, and phenyl; and n=1-4.

Preferably each $R^1$ is independently selected from the group consisting of methyl and ethyl and each $R^2$ is independently selected from the group consisting of hydrogen, methyl, ethyl, propyl, iso-propyl, n-butyl, iso-butyl, tert-butyl, allyl and phenyl.

Preferably the hydrazinosilane is reacted with nitrogen source selected from the group consisting of nitrogen, ammonia, hydrazine, and mixtures thereof for silicon nitride depositions.

Although many hydrazinosilanes will be acceptable for silicon nitride film precursors, the following Table 1 illustrates exemplary hydrazinosilanes which are contemplated.

TABLE 1

Exemplary Hydrazinosilanes

A

B

C

TABLE 1-continued

Exemplary Hydrazinosilanes

D

E

F

G

H

I

Appropriate hydrazinosilanes include: (A) Bis(1,1-dimethylhydrazino) methylsilane, (B) Tris(1,1-dimethylhydrazino)silane, (C) Tris(1,1-dimethylhydrazino) t-butylsilane, (D) Tris(1,1-dimethylhydrazino)s-butylsilane, (E) Tris (1, 1-dimethylhydrazino)ethylsilane, (F) Bis(1,1-dimethylhydrazino)ethylsilane, (G) Bis(1, 1-dimethylhydrazino)Iso-propylsilane, (H) Bis(1,1-dimethylhydrazino)allylsilane, (I) Bis(1, 1-dimethylhydrazino)silane, (Y) Tetrakis(1, 1-dimethylhydrazino)silane, N,N',N"-Tris(dimethylamino)cyclotrisilazane, N,N',N",N'"-Tetrakis(dimethylamino)cyclotrisilazane, Tris(1, 1-dimethylhydrazino)Iso-propylsilane, and Tris(1, 1-dimethylhydrazino)allylsilane. Lower molecular weight hydrazinosilanes are preferred and non-cyclic hydrazinosilanes are preferred over cyclic hydrazinosilanes. These compounds are synthesized by the reaction of corresponding chlorosilanes with dialkylhydrazine using organoamines, such as triethylamine as a base.

Silicon nitride films on the surface of semiconductor substrates can be generated from these compounds in a chemical vapor deposition process in the temperature range of 100° C.-800° C. and in the pressure range of $10^{-5}$-760 Torr. The thin film formed are excellent in step coverage inside trenches and in thickness uniformity of wafers.

4) The hydrazinosilanes give excellent deposition uniformities.
5) When compared to other available precursors, such as silanes with ligands of diamino, dimethylamino and other alkylamines, the deposition temperature using these precursors can be lower by 150 to 300° C.

A comparison of other precursor deposition temperatures, precursor and film properties are given in Table 2.

TABLE 2

| Precursors | Vapor Pressure (Torr @ ° C.) | Deposition Temp. (° C.) | Precursor and Film Properties |
|---|---|---|---|
| $SiH_4$ + $NH_3$ | Gas at ambient | 200–400 Plasma process | Pyrophoric gas. Gas phase reaction. Silicon rich at lower temperatures. Films may contain hydrogen. |
| $Cl_2SiH_2$ + $NH_3$ | Gas at ambient | >750 | Corrosive gas. Direct Si—Cl bonds. Chlorine contamination. Ammonium chloride as byproduct. |
| $(C_2H_5)_2SiH_2$ + $NH_3$ | 100 at 20 | 650–725 | Poor uniformities. Direct Si—C bonds. Direct Si—Cl bonds. Carbon impurities in the films >2%. May require cage boats and temperature ramping. |
| $(t\text{-}C_4H_9)_2SiH_2$ + $NH_3$ | 20.5 at 20 | 600–700 | Direct Si—C bonds. Carbon content(10at %)in the films. |
| $[(CH_3)_2N]_3SiR$ + $NH_3$ R = H or CH3 | 16 at 25 | 700–1000 | Direct Si—C bonds. Carbon content in the films >2% and require high ammonia to source ratios (30:1). Poor uniformities of >5%. |
| $(t\text{-}C_4H_9NH)_2SiH_2$ | 7.5 at 45 | 500–1000 | No Si—C bonds, no carbon contamination, good uniformity and high deposition rate. |
| Hydrazinosilanes | 25 at 46 to 1 at 56 | 100–800 | Good uniformities, little or no carbon, very high deposition rates. |

Due to the nitrogen rich character of the molecules, silicon nitride films can be generated with or without the inclusion of ammonia or other additive.

The deposited films have superior uniformities and are free of ammonium chloride and chlorine contamination. The hydrazinosilanes have the property to deposit silicon nitride at temperatures well below that of the dichlorosilane and ammonia process by LPCVD.

The remarkable advantages of hydrazinosilanes may be attributable to the inherent property of the ligands in the precursors. During pyrolysis of these precursors, these ligands may eliminate readily as volatile products. Other advantages of hydrazinosilanes can be summarized as follows:

1) They are non-pyrophoric volatile stable liquids or low melting point volatile solids.
2) They do not have any chlorine in the molecules. The Si—Cl bonds in dichlorosilane lead to the formation of ammonium chloride which deposits in the back end of the tube or on the walls of single wafer reactors and requires frequent cleaning.
3) The resulting silicon nitride films were relatively carbon free, as indicated by Rutherford Backscattering Spectrometry.

The following Table 3 lists compounds that were investigated during the development of the present invention, including compounds that were synthesized, used as precursors for $SiN_xO_y$ films, and additionally those that are merely contemplated for utility in the present invention.

TABLE 3

| Chemical Name | Structure |
|---|---|
| Bis(1,1-dimethylhydrazino) methylsilane | |
| Tris(1,1-dimethylhydrazino) t-butylsilane | |

TABLE 3-continued

| Chemical Name | Structure |
|---|---|
| Tris(1,1-dimethylhydrazino) s-butylsilane |  |
| Tris(1,1-dimethylhydrazino) ethylsilane |  |
| Bis(1,1-dimethylhydrazino) ethylsilane |  |
| Tris(1,1-dimethylhydrazino) silane |  |
| Bis(1,1-dimethylhydrazino) Iso-propylsilane |  |
| Bis(1,1-dimethylhydrazino) allylsilane |  |
| Bis(1,1-dimethylhydrazino) silane |  |
| Tetrakis(1,1-dimethylhydrazino) silane |  |
| N,N',N''-Tris(dimethylamino)cyclotrisilazane |  |
| N,N',N'',N'''-Tetrakis(dimethylamino)cyclotrisilazane |  |
| Tris(1,1-dimethylhydrazino) Iso-propylsilane |  |
| Tris(1,1-dimethylhydrazino) Allylsilane |  |

To form silicon nitride films, the hydrazinosilane and optionally ammonia (or nitrogen or hydrazine) are allowed to react in the reactor tube at an elevated temperature (preferably 100° C.-800° C., but the temperature could be less or greater than this range). Reaction may occur either on the surface or very close to the wafer surface to deposit a thin silicon nitride film. If the reaction occurs in the gas phase (a homogeneous reaction) then clusters of silicon nitride are formed. Such cases are typical in silane and ammonia process. When the reaction occurs at the wafer surface then the resulting films are of superior uniformities. Thus, one important requirement for CVD application is the degree to which heterogeneous reactions are favored over gas phase reactions.

The CVD process can be grouped into a) a gas-phase process and b) a surface reaction process. The gas phase phenomenon is the rate at which gases impinge on the substrate. This is modeled by the rate at which gases cross the boundary layer that separates the bulk regions of flowing gas and substrate surface. Such transport processes occur by gas-phase diffusion, which is proportional to the diffusivity of the gas and concentration gradient across the boundary layer. Several surface processes can be important when the gases reach the hot surface, but the surface reaction, in general, can be modeled by a thermally activated phenomenon which proceeds at a rate which is a function of the frequency factor, the activation energy, and the temperature.

The surface reaction rate increases with increasing temperature. For a given surface reaction, the temperature may rise high enough so that the reaction rate exceeds the rate at which reactant species arrive at the surface. In such cases, the reaction cannot proceed any more rapidly than the rate at which reactant gases are supplied to the substrate by mass transport. This is referred to as a mass-transport limited deposition process. At lower temperatures, the surface reaction rate is reduced, and eventually the concentration of reactants exceeds the rate at which they are consumed by the surface reaction process. Under such conditions the deposition rate is reaction rate limited. Thus, at high temperatures, the deposition is usually mass-transport limited, while at lower temperatures it is surface-reaction rate-limited. In actual processes, the temperature at which the deposition condition moves from one of these growth regimes to the other is dependent on the activation energy of the reaction, and the gas flow conditions in the reactor. Thus, it is difficult to extrapolate process conditions or results from one pressure regime or temperature regime to another.

In processes that are run under reaction rate-limited conditions, the temperature of the process is an important parameter. That is, uniform deposition rates throughout a reactor require conditions that maintain a constant reaction rate. This, in turn, implies that a constant temperature must exist everywhere on all wafer surfaces. On the other hand, under such conditions, the rate at which reactants reach the surface is not important, since their concentration does not limit the growth rate. Thus, it is not as critical that a reactor be designed to supply an equal flux of reactants to all locations of a wafer surface. It should be appreciated that in LPCVD reactors, wafers can be stacked at very close spacing because such systems operate in a reaction rate limited mode. The reason for this is as follows: Under the low pressure of an LPCVD reactor ~1 torr, the diffusivity of the gas species is increased by a factor of 1000 over that at atmospheric pressure, and this is only partially offset by the fact that the boundary layer, the distance across which the reactants must diffuse, increases by less than the square root of the pressure. The net effect is that there is more than an order of magnitude increase in the transport of reactants to and byproducts away from the substrate surface, and the rate-limiting step is thus the surface reaction.

Low pressure chemical vapor deposition processes (LPCVD) involve chemical reactions that are allowed to take place in the pressure range of $10^{-5}$ Torr to 760 Torr. The chemical vapor deposition (CVD) process can be described in the following sequence of steps at a given temperature, pressure and ratio of the reactants:

1) Reactants are introduced into the reaction chamber and may be diluted with inert gases, if needed;
2) The reactants are allowed to diffuse to the substrate;
3) The reactants are adsorbed on the substrate, and the adsorbed molecules undergo migration; and
4) Chemical reactions occur on the surface, and the gaseous byproducts of the reaction are desorbed, leaving behind the deposited film. The reactions are initiated by several methods; e.g., thermal or photons. Thermal energy is used in the LPCVD process.

Horizontal tube hot wall reactors are the most widely used for LPCVD in VLSI manufacturing. They are employed for depositing poly-Si, silicon nitride, undoped and doped silicon dioxide films. These reactors are used extensively because they are economical, have high throughputs, their deposited films are uniform and they can accommodate large diameter wafers (6"-12"). Their main disadvantages are susceptibility to particulate contamination and low deposition rates.

The vertical tube hot wall reactors are now replacing the horizontal reactors for many processes for 200 mm diameter and larger wafers. Several other types of reactors are in use with injection schemes to avoid the wafer-to-wafer reactant depletion effects. They require no temperature ramping, produce highly uniform depositions and reportedly achieve low particulate contamination.

To induce the low pressure conditions in the reactor, an appropriate vacuum system is necessary. An appropriate vacuum system may consist of a rotary vane pump/roots blower combination and various cold traps. The reactor pressure is controlled by a capacitance manometer feedback to a throttle valve controller. Our survey reactor loading consists of eighty 100 mm diameter silicon wafers at 9 mm spacing in standard diffusion boats. The boats are positioned on a sled, so that the wafers centers are slightly above the center of the reaction tube. This produces a uniform conductance around the wafer peripheries by compensating for conductance restrictions caused by the boats and the sled. The temperature uniformity across the wafer load is measured by an internal multi-junction thermocouple. Deposition uniformity down the wafer load is improved by a temperature ramp. Gases and vapors are fed from around a load door or through injectors.

Hydrazinosilanes are non-pyrophoric volatile liquids or low melting point volatile solids that are safer to handle than silane and dichlorosilane. The deposition process is carried out at preferably $10^{-5}$ Torr-760 Torr in the temperature range of preferably 100° C. to 800° C. using vapors from hydrazinosilane and optionally ammonia. Optionally, an inert gas diluent, such as nitrogen or argon, can be used to dilute and control the rate of reaction. The molar feed ratio of ammonia to hydrazinosilane is used to modify the film properties and we have used from 0 to over 100:1 ammonia to hydrazinosilane.

EXAMPLE 1

Synthesis of Bis(1,1-dimethylhydrazino)methylsilane

In a 2000 ml three-neck round bottom flask equipped with two addition funnels, a condenser, and a mechanical stirrer, 500 ml of hexane and 303 g of triethylamine were added. With the cooling of an ice bath and protection of nitrogen atmosphere, a solution of 115 g methyldichlorosilane in 100 ml hexane and a solution of 150 g 1,1-dimethylhydrazine in 50 ml hexane were added through two addition funnels at about equal rates. The reaction mixture was then allowed to warm to room temperature and stirred overnight. In nitrogen atmosphere, the reaction mixture was filtered and the solid amine salt was washed with hexane. The solvent and excess amines were removed by vacuum distillation. Vacuum distillation produced 125 g of Bis(1,1-dimethylhydrazino) methylsilane, boiling point 45° C./22 Torr.

EXAMPLE 2

Synthesis of Bis(1,1-dimethylhydrazino)ethylsilane

In a 5000 ml three-neck round bottom flask equipped with two addition funnels, a condenser, and a mechanical stirrer, 1500 ml of hexane and 450 g of triethylamine were added. With the cooling of an ice bath and protection of nitrogen atmosphere, a solution of 200 g ethyltrichlorosilane in 500 ml hexane and 196 g 1,1-dimethylhydrazine were added through two addition funnels at about equal rates. The reaction mixture was then allowed to warm to room temperature and stirred overnight. In nitrogen atmosphere, the reaction mixture was filtered and the solid amine salt was washed with hexane. The solvent and excess amines were removed by vacuum distillation. Vacuum distillation produced 154 g of Bis(1,1-dimethylhydrazino)ethylsilane, boiling point 40° C./10 Torr.

EXAMPLE 3

Synthesis of Tris(1,1-dimethylhydrazino)-t-butylsilane

In a 2000 ml three-neck round bottom flask equipped with two addition funnels, a condenser, and a mechanical stirrer, 800 ml of hexane and 125 g of triethylamine were added. With the cooling of an ice bath and protection of nitrogen atmosphere, a solution of 48 g t-butyltrichlorosilane in 100 ml hexane and a solution of 50 g 1,1-dimethylhydrazine in 100 ml hexane were added through two addition funnels at about equal rates. The reaction mixture was then allowed to warm to room temperature and stirred overnight. In nitrogen atmosphere, the reaction mixture was filtered and the solid amine salt was washed with hexane. The solvent and excess amines were removed by vacuum distillation. Vacuum distillation produced 30 g of Tris(1,1-dimethylhydrazino)-t-butylsilane, boiling point 56° C./2 Torr. $^1$H NMR 1.19 (s, 9H), 2.34 (s, 18H).

EXAMPLE 4

Synthesis of Tris(1,1-dimethylhydrazino)-iso-butylsilane

In a 5000 ml three-neck round bottom flask equipped with two addition funnels, a condenser, and a mechanical stirrer, 1500 ml of hexane and 400 g of triethylamine were added. With the cooling of an ice bath and protection of nitrogen atmosphere, a solution of 200 g iso-butyltrichlorosilane in 200 ml hexane and 240 g 1,1-dimethylhydrazine were added through two addition funnels at about equal rates. The reaction mixture was then allowed to warm to room temperature and stirred overnight. In nitrogen atmosphere, the reaction mixture was filtered and the solid amine salt was washed with hexane. The solvent and excess amines were removed by vacuum distillation. Vacuum distillation produced 170 g of Tris(1,1-dimethylhydrazino)-iso-butylsilane, boiling point 61° C./2 Torr.

EXAMPLE 5

Synthesis of Tris(1,1-dimethylhydrazino)ethylsilane

In a 5000 ml three-neck round bottom flask equipped with two addition funnels, a condenser, and a mechanical stirrer, 2000 ml of hexane and 500 g of triethylamine were added. With the cooling of an ice bath and protection of nitrogen atmosphere, a solution of 190 g ethyltrichlorosilane in 100 ml hexane and 290 g 1,1-dimethylhydrazine were added through two addition funnels at about equal rates. The reaction mixture was then allowed to warm to room temperature and stirred overnight. In nitrogen atmosphere, the reaction mixture was filtered and the solid amine salt was washed with hexane. The solvent and excess amines were removed by vacuum distillation. Vacuum distillation produced 153 g of Tris(1,1-dimethylhydrazino)ethylsilane, boiling point 51° C./2 Torr.

EXAMPLE 6

Synthesis of Tetrakis(1,1-dimethylhydrazino)silane

In a 5000 ml three-neck round bottom flask equipped with two addition funnels, a condenser, and a mechanical stirrer, 2000 ml of hexane and 600 g of 1,1-dimethylhydrazine were added. With the cooling of dry ice bath and protection of nitrogen atmosphere, a solution of 170 g silicon tetrachloride in 350 ml hexane was slowly added. The reaction mixture was then allowed to warm to room temperature and stirred overnight. In nitrogen atmosphere, the reaction mixture was filtered and the solid salt was washed with hexane. The solvent was partially removed under reduced pressure and the solution was concentrated to the volume of about 1 liter. Once some solid started to precipitate from the solution, the solution was placed in a refrigerator. The solid product was filtered and dried under vacuum. 185 g of tetrakis(1,1-dimethylhydrazino)silane was obtained, melting point 63° C.

EXAMPLE 7

LPCVD of Tris(dimethylhydrazino)tert-butylsilane and Ammonia

The process involves pyrolysis of tris(dimethylhydrazino)-tert-butylsilane (TDMHtBS) or reaction of the precursor with ammonia under LPCVD conditions (low pressure range of 20 mTorr-2 Torr). The precursor and ammonia (or nitrogen diluent) are introduced into the heated reactor (200-800° C.) via injectors placed at the door. The reactants are flowed over wafers into the evacuated chamber. The ammonia (or nitrogen) to silicon source is kept at a ratio in the range of 1:1-10:1. A continuous film of silicon nitride is deposited upon the surface of a silicon wafer. These films are suitable for integrated circuit manufacture. A typical run was carried out in a 150 mm hot wall LPCVD horizontal tube reactor, although the apparatus configuration is not critical. The process involves loading the quartz reactor with 75 to 100 silicon wafers; evacuating the system; letting the wafers come to a desired temperature at which the deposition will be carried out. The energy required for this reaction can be supplied by simple resistive heating. This is advantageous because the equipment is less expensive, and one avoids radiative film damage often associated with plasma reactors.

A typical run flowed 30 sccm of TDMHtBS with 60 sccm NH$_3$ at 500° C. and 400 mTorr. The average deposition rate was 11.5 Å/min over 80 wafers. The films are characterized by infrared spectroscopy and refractive index. FT-IR spectrum is consistent with silicon nitride films deposited from other known nitride precursors e.g. dichlorosilane+ammonia. There are moderate absorption bands in the Si—H stretching region at 2100 cm$^{-1}$ and a strong Si—N stretch at 870 cm$^{-1}$. However, these films are somewhat porous at lower temperatures and low ammonia ratios, so there is some oxidation after removal from the reactor. Refractive indices for these films were measured by ellipsometry at 632.4 nm and the refractive indices fell from >1.7 to about 1.6 due to porosity. Silicon nitride films were characterized by Rutherford Backscattering analysis. Silicon, carbon, nitrogen and oxygen content for these films were determined. The composition of silicon nitride was about 1:1.1 silicon to nitrogen after depositions. The composition of these films was uniform throughout the depth of the films. Carbon was at the detection limit (1 to 2 atomic %), but much of this was from air contamination.

EXAMPLE 8

LPCVD of Tris(dimethylhydrazino)ethylsilane and Ammonia

The process involves pyrolysis of tris(dimethylhydrazino) ethylsilane (TDMHES) or reaction with ammonia under LPCVD conditions (low pressure range of 20 mTorr-2 Torr) similar to that in Example 7. A typical run flowed 30 sccm of TDMHES with 60 sccm $NH_3$ at 500° C. and 400 mTorr. The average deposition rate was 20 Å/min over 80 wafers. RBS analysis showed these films are silicon rich, a prerequisite for obtaining low stress nitrides for MEMS applications.

EXAMPLE 9

LPCVD of Bis(dimethylhydrazino)methylsilane and Ammonia

The process involves pyrolysis of bis(dimethylhydrazino) methylsilane (BDMHMS) or reaction with ammonia under LPCVD conditions (low pressure range of 20 mTorr-2 Torr) similar to that in Example 7. A typical run flowed 70 sccm of BDMHMS with 120 sccm $N_2$ at 500° C. and 500 mTorr. The average deposition rate was 8.5 Å/min over 80 wafers. FTIR analysis showed these films were nitrogen-rich and low density with the Si—N stretch at 870 $cm^{-1}$.

EXAMPLE 10

LPCVD of Bis(dimethylhydrazino)ethylsilane and Ammonia

Figure 1:
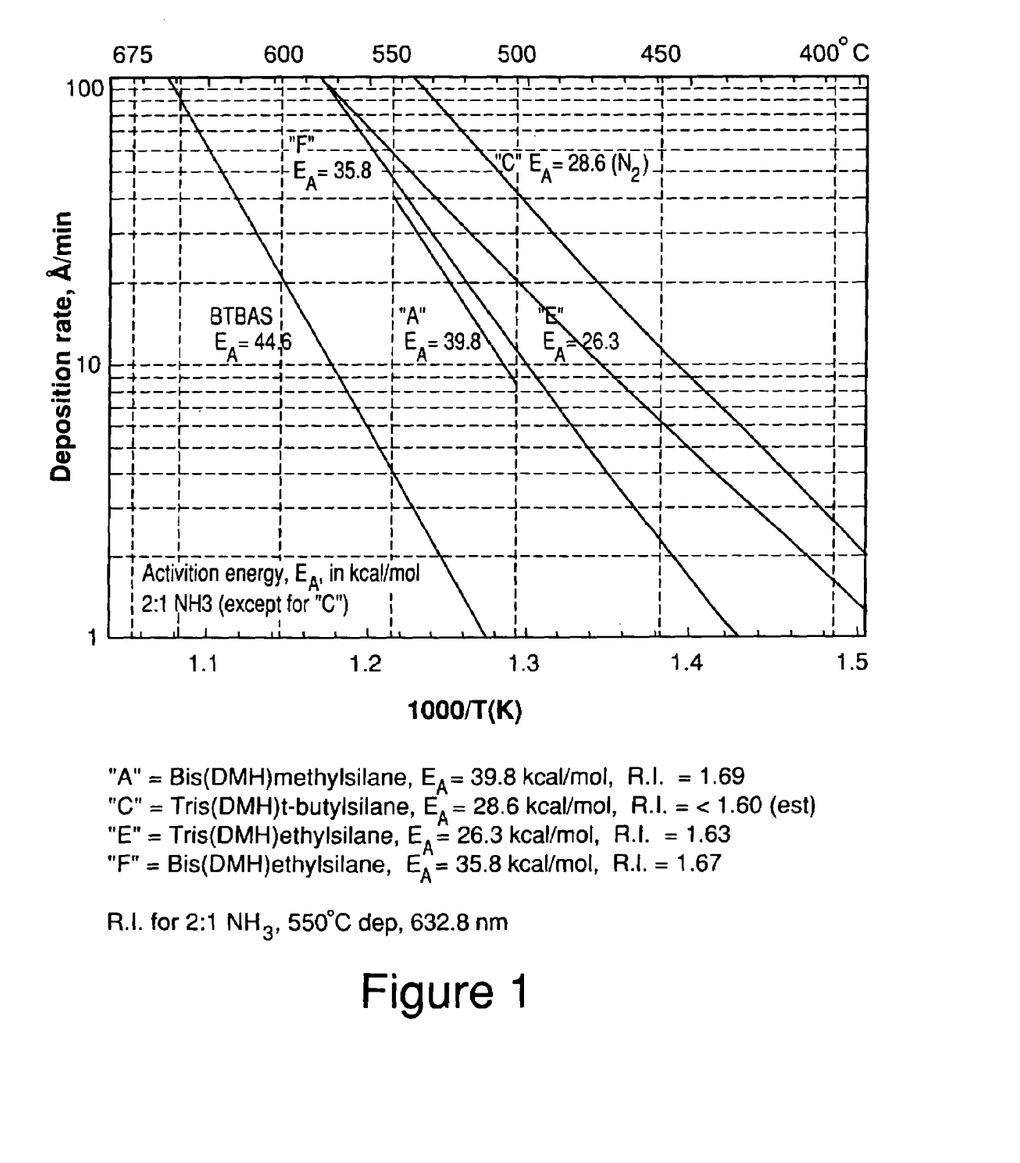
FIG. 1 is a graph of deposition rate versus the inverse of temperature for a number of silicon nitride precursors, including BTBAS ("bis(t-butylamino)silane").
Figure 2:
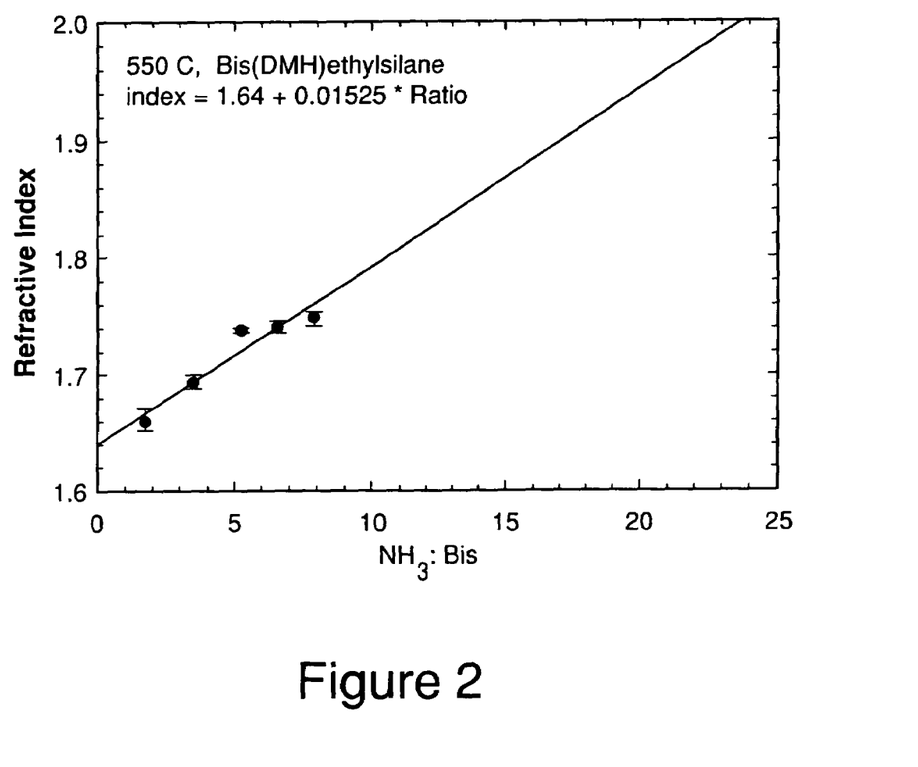
FIG. 2 is a graph of refractive index versus the ratio of ammonia to bis(dimethylhydrazino)ethylsilane.
Figure 3A:
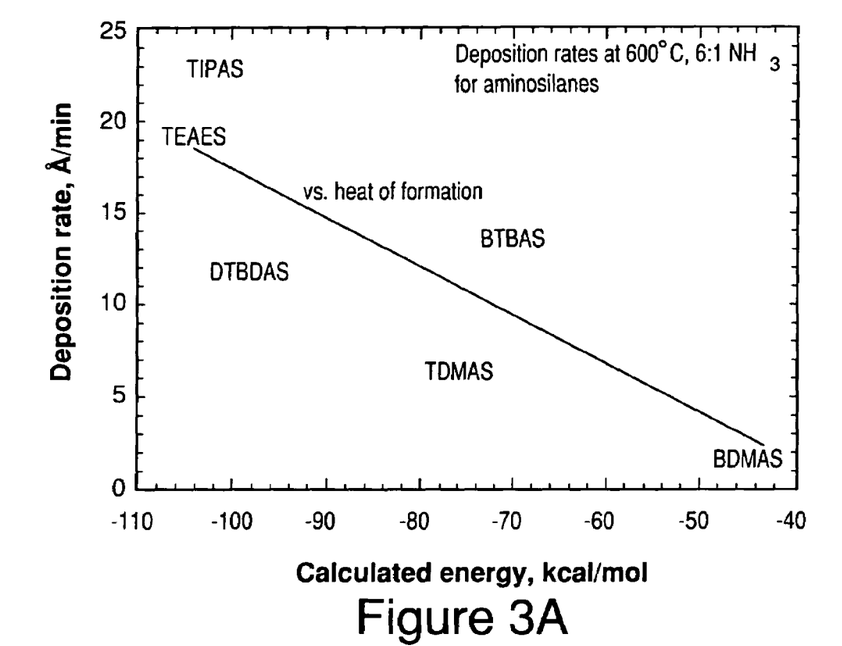
FIG. 3A is a graph of deposition rate versus calculated energy (−110 kcal/mol to −40 kcal/mol) for various aminosilanes.
Figure 3B:
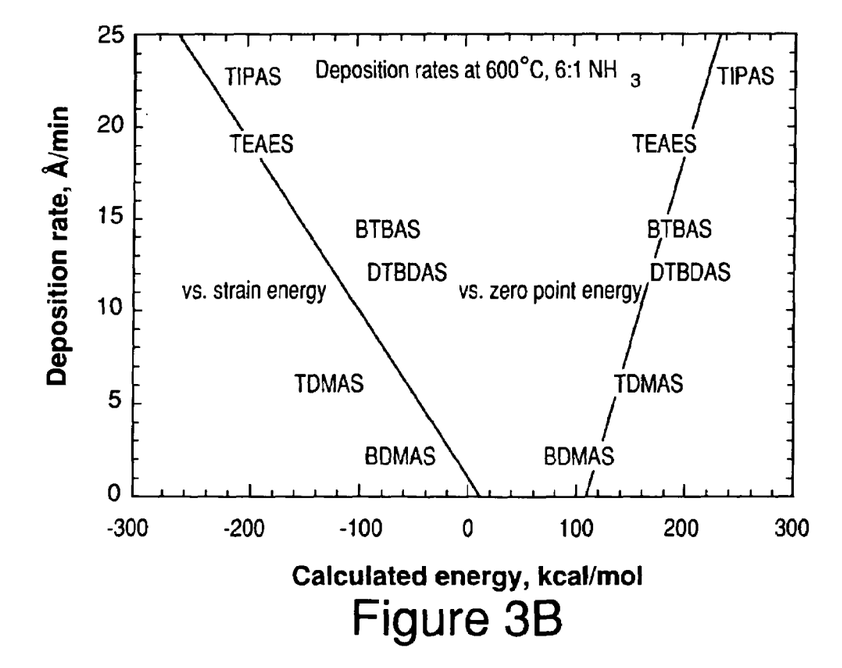
FIG. 3B is a graph of deposition rate versus calculated energy (−300 kcal/mol to 300 kcal/mol) for various aminosilanes.
Figure 4A:
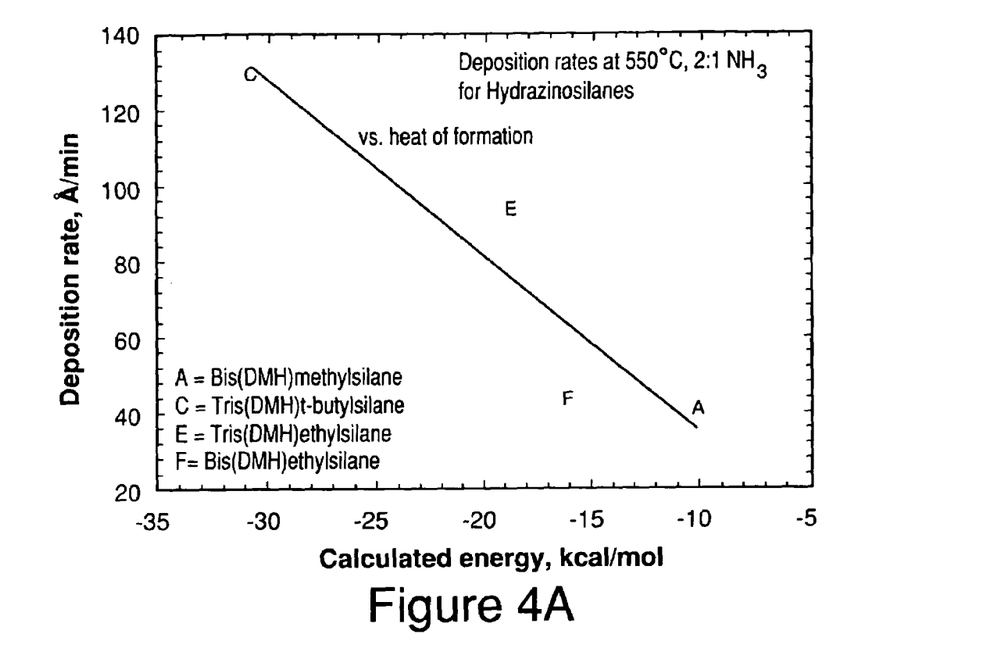
FIG. 4A is a graph of deposition rate versus calculated energy (−35 kcal/mol to −5 kcai/mol) for various hydrazinosilanes.
Figure 4B:
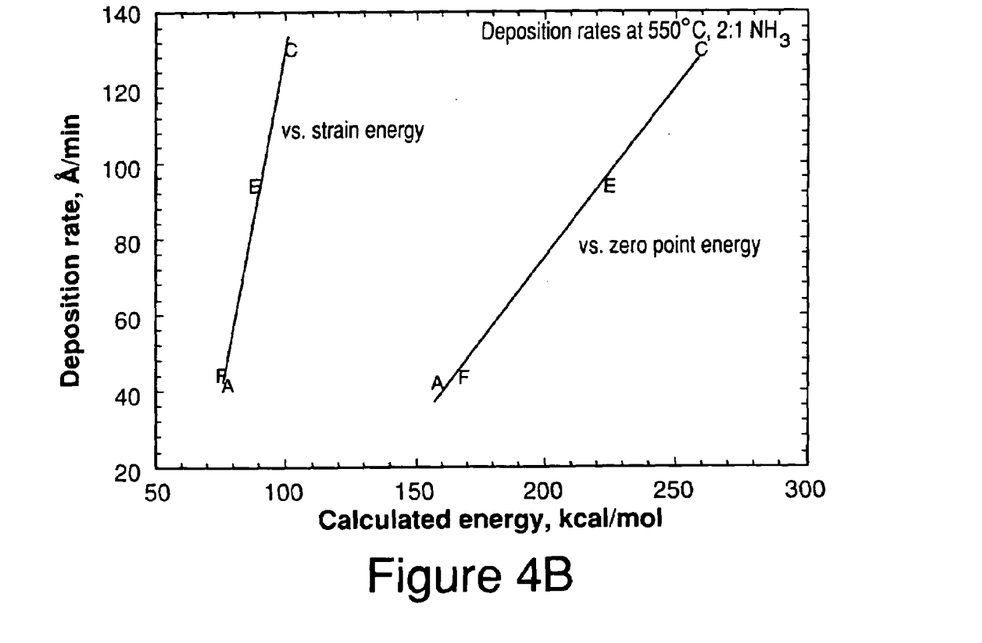
FIG. 4B is a graph of deposition rate versus calculated energy (50 kcal/mol to −300 kcal/mol) for various hydrazinosilanes.

The process involves pyrolysis of bis(dimethylhydrazino) ethylsilane (BDMHES) or reaction with ammonia under LPCVD conditions (low pressure range of 20 mTorr-2Torr) similar to that in Example 7. A typical run flowed 34 sccm of BDMHES with 60 sccm $NH_3$ at 500° C. and 400 mTorr. The average deposition rate was 11.5 Å/min over 80 wafers. RBS analysis showed these films were silicon nitride. Ellipsometry showed these depositions were of low to medium density with refractive indices of 1.75 that did not change with time, significantly. Additional deposition rates versus inverse temperatures are shown in FIG. 1 where they are compared to deposition results using aminosilanes.

EXAMPLE 11

PECVD of Bis(dimethylhydrazino)ethylsilane and Ammonia

Figure 5:
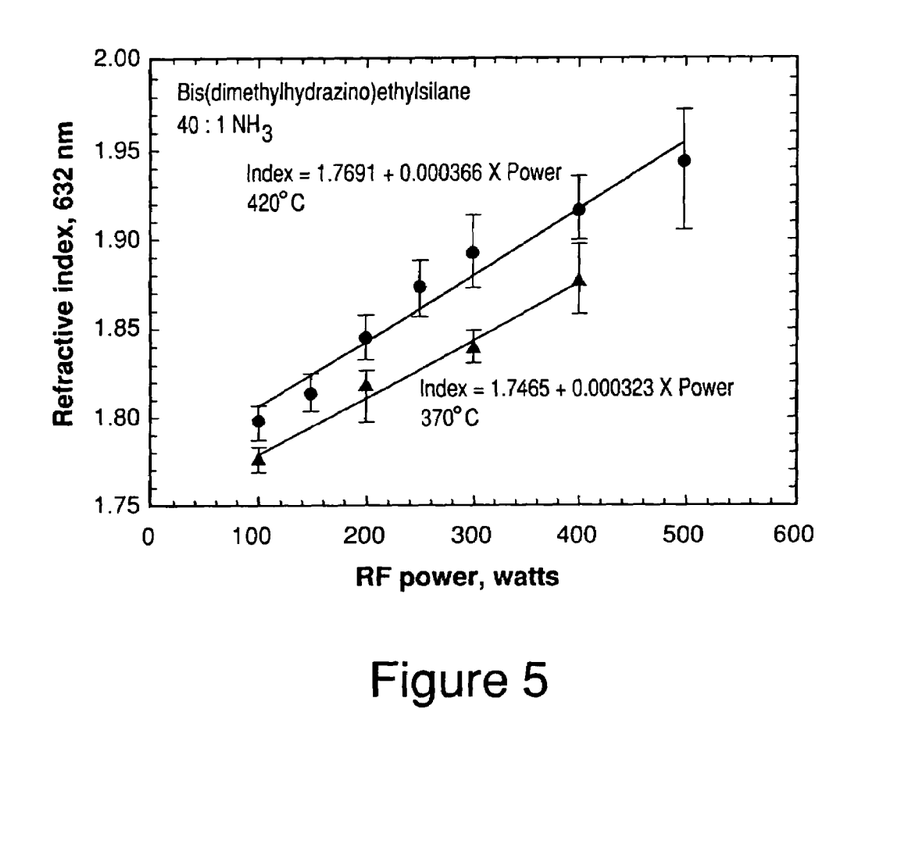
FIG. 5 is a refractive index versus RF power for plasma enhanced chemical vapor deposition using bis(dimethylamino)ethylsilane.

The process involves plasma-enhanced chemical vapor deposition using bis(dimethylhydrazino)ethylsilane (BDMHES) and ammonia in a single-wafer plasma reactor. A typical run flowed 7 sccm of BDMHES with 300 sccm $NH_3$ at 420° C. and 1000 mTorr. For an average RF power of 2.2 watts/$cm^2$, the average deposition rate was 85 Å/min with a refractive index of 1.92. FTIR showed these depositions were of high density with the Si—N stretch at 860 $cm^{-1}$. Additional data is shown in FIG. 5 for depositions at nominal temperatures of 370° C. and 420° C.

EXAMPLE 12

LPCVD of Bis(dimethylhydrazino)ethylsilane and Ammonia

The process involves low pressure chemical vapor deposition in a single wafer reactor using bis(dimethylhydrazino) ethylsilane (BDMHES) and ammonia. A typical run flowed 5.5 sccm of BDMHES with 11 sccm $NH_3$ at 370° C. and 2000 mTorr. The average deposition rate was 15 Å/min with a refractive index of 1.73. FTIR showed these depositions were of medium to low density with the Si—N stretch at 872 $cm^{-1}$.

Figure 6:
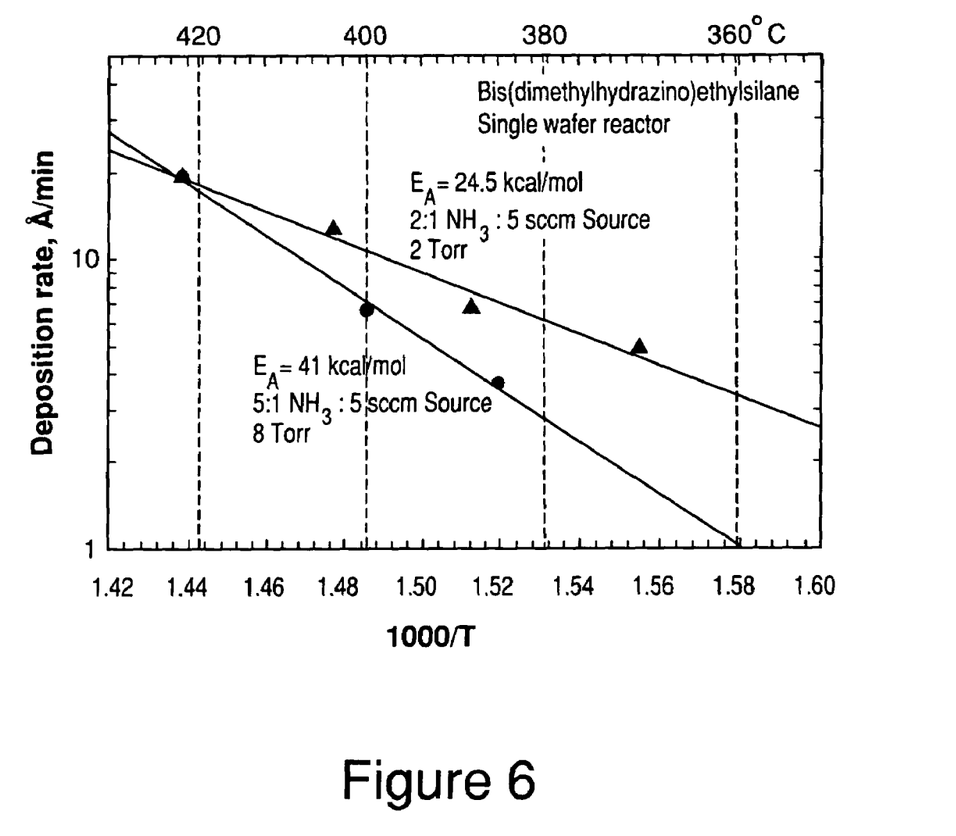
FIG. 6 is an Arrhenius plot of single layer depositions using bis(dimethylamino)ethylsilane.

Additional deposition data is shown for this compound ("F") in the single wafer reactor at 2 Torr and 8 Torr process pressures in FIG. 6.

The present invention has been set forth with regard to several embodiments, however the full scope of the present invention should be ascertained from the claims which follow.

The invention claimed is:

1. A precursor composition for use in the chemical vapor deposition of a material selected from the group consisting of silicon oxynitride, silicon nitride, and silicon oxide, the composition comprising:

a hydrazinosilane of the formula:

where each $R^1$ is independently selected from alkyl groups of $C_1$ to $C_6$; each $R^2$ is independently selected from the group consisting of hydrogen, alkyl, vinyl, allyl, and phenyl; and n=1-4; and a nitrogen-containing compound selected from the group consisting of ammonia, nitrogen, hydrazine, and mixtures thereof.

2. The precursor composition of claim 1 wherein nitrogen-containing compound is ammonia.

3. The precursor composition of claim 2 wherein the molar ratio of ammonia to the hydrazinosilane is greater than zero.

4. The precursor composition of claim 1 wherein each $R^1$ is independently selected from the group consisting of methyl and ethyl; and each $R^2$ is independently selected from the group consisting of hydrogen, methyl, ethyl, propyl, iso-propyl, n-butyl, iso-butyl, tert-butyl, allyl and phenyl.

5. The precursor composition of claim 1 wherein the hydrazinosilane is selected from the group consisting of: Bis(1, 1-dimethylhydrazino)methylsilane, Tris(1, 1-dimethylhydrazino)silane, Tris(1, 1-dimethylhydrazino)-t-butylsilane, Tris(1, 1-dimethylhydrazino)s-butylsilane, Tris(1, 1-dimethylhydrazino)ethylsilane, Bis(1, 1-dimethylhydrazino)ethylsilane, Bis(1, 1-dimethylhydrazino)lso-propylsilane, Bis(1, 1-dimethylhydrazino)allylsilane, Bis(1, 1-dimethylhydrazino)silane, Tetrakis(1, 1-dimethylhydrazino)silane, N,N',N"-Tris(dimethylamino)cyclotrisilazane, N,N',N",N'''-Tetrakis(dimethylamino)cyclotrisilazane, Tris(1, 1-dimethylhydrazino) Iso-propylsilane, Tris(1, 1-dimethylhydrazino)allylsilane and mixtures thereof.

6. The precursor composition of claim 1 wherein the hydrazinosilane is Tris(1, 1-dimethylhydrazino)silane.

7. The precursor composition of claim 1 wherein the hydrazinosilane is Tris(1, 1-dimethylhydrazino)-t-butylsilane.

8. The precursor composition of claim 1 wherein the hydrazinosilane is Tris(1, 1-dimethylhydrazino)-s-butylsilane.

9. The precursor composition of claim 1 wherein the hydrazinosilane is Bis(1, 1-dimethylhydrazino)-iso-propylsilane.

10. The precursor composition of claim 1 wherein the hydrazinosilane is Bis(1, 1-dimethylhydrazino)allylsilane.

11. The precursor composition of claim 1 wherein the hydrazinosilane is Bis(1, 1-dimethylhydrazino)silane.

12. The precursor composition of claim 1 wherein the hydrazinosilane is Tetrakis(1, 1-dimethylhydrazino)silane.

13. The precursor composition of claim 1 wherein the hydrazinosilane is N,N',N"-Tris(dimethylamino)cyclotrisilazane.

14. The precursor composition of claim 1 wherein the hydrazinosilane is Tris(1, 1-dimethylhydrazino)-iso-propylsilane.

15. The precursor composition of claim 1 wherein the hydrazinosilane is Tris(1, 1-dimethylhydrazino)allylsilane.

16. A precursor composition for use in the chemical vapor deposition of a material selected from the group consisting of silicon oxynitride, silicon nitride, and silicon oxide, the composition consisting essentially of:
  ammonia; and
  a hydrazinosilane selected from the group consisting of: Bis(1, 1-dimethylhydrazino)methylsilane, Tris(1, 1-dimethylhydrazino)silane, Tris(1, 1-dimethylhydrazino)-t-butylsilane, Tris(1, 1-dimethylhydrazino)s-butylsilane, Tris(1, 1-dimethylhydrazino)ethylsilane, Bis(1, 1-dimethylhydrazino)ethylsilane, Bis(1, 1-dimethylhydrazino)Iso-propylsilane, Bis(1, 1-dimethylhydrazino)allylsilane, Bis(1, 1-dimethylhydrazino)silane, Tetrakis(1, 1-dimethylhydrazino)silane, N,N',N"-Tris(dimethylamino)cyclotrisilazane, N,N',N",N'"-Tetrakis(dimethylamino)cyclotrisilazane, Tris(1, 1-dimethylhydrazino)Iso-propylsilane, Tris(1, 1-dimethylhydrazino)allylsilane and mixtures thereof.

17. The precursor composition of claim 16 wherein the hydrazinosilane is Tris(1,1-dimethylhydrazino)tert-butylsilane.

18. The precursor composition of claim 16 wherein the hydrazinosilane is Tris(1,1-dimethylhydrazino)ethylsilane.

19. The precursor composition of claim 16 wherein the hydrazinosilane is Bis(1,1-dimethylhydrazino)ethylsilane.

* * * * *